United States Patent [19]

Barrett et al.

[11] 4,329,588
[45] May 11, 1982

[54] POLARIZATION SWITCHED OPTICAL FILTERING FOR TRANSVERSE TOMOGRAPHY

[75] Inventors: Harrison H. Barrett; William Swindell, both of Tucson, Ariz.; John E. Greivenkamp, Jr., Cincinnati, Ohio

[73] Assignee: University Patents, Inc., Norwalk, Conn.

[21] Appl. No.: 132,563

[22] Filed: Mar. 21, 1980

[51] Int. Cl.$^3$ .............................................. A61B 6/00
[52] U.S. Cl. ................................ 250/445 T; 250/225; 250/237 G; 350/162 SF; 364/414; 364/822
[58] Field of Search ............... 250/237 G, 237 R, 225, 250/445 T; 350/162 SF; 364/822, 414

[56] References Cited

U.S. PATENT DOCUMENTS

| 2,281,931 | 5/1942 | Frank | 250/445 T |
| 3,027,806 | 4/1962 | Koelsch, Jr. et al. | 250/225 |
| 4,023,036 | 5/1977 | Barrett et al. | 250/237 R |
| 4,081,673 | 3/1978 | Swindell et al. | 250/237 R |

OTHER PUBLICATIONS

Holladay et al., "Phase Control by Polarization in Coherent Spatial Filtering", J.O.S.A., vol. 56, No. 7, Jul. 1966, pp. 869-872.

Primary Examiner—Alfred E. Smith
Assistant Examiner—T. N. Grigsby
Attorney, Agent, or Firm—Martin Novack

[57] ABSTRACT

The disclosure is directed to an apparatus and method for generating a two-dimensional back-projected image of a slice of an object, and also to an optical filtering apparatus and method which, inter alia, is useful therein. Successive beams of light are generated, each having a narrow elongated cross-section with an optical intensity that is a function of the density characteristic of the slice of the object as measured at a particular relative rotational angle. The beams are optically filtered and spread in a direction transverse to their length. Optical filtering with a filter function having both positive and negative components is preferably performed using a single-channel time modulated technique. A television camera receives the spread filtered beams. Relative rotation is effected between the beams and the camera, the rotation being related to the relative rotational angles of the object associated with the generation of the successive beams of light. A digital frame store accumulates the intensities sensed at elemental areas of the image sensing means. The accumulated intensities comprise a two-dimensional back-projected image of the slice of the object which can then be displayed on a television display. In a further form of the disclosure, back-projected images are obtained using an optical "loop" processor which employs a single-channel time modulated filtering technique.

9 Claims, 11 Drawing Figures

POLARIZATION SWITCHED OPTICAL FILTERING FOR TRANSVERSE TOMOGRAPHY

DESCRIPTION

1. Technical Field

This invention relates to X-ray tomography and, more particularly, to an apparatus and method for imaging cross-sections of objects using transverse tomography techniques. The subject matter hereof is related to subject matter disclosed in copending U.S. Application Ser. No. 132,562 entitled "Transverse Tomography With Optical Filtering", filed of even date herewith.

2. Background Art

Using conventional X-ray imaging techniques, a shadow view of a body under examination can be produced, but it does not contain information concerning the depth of details in the body. In many cases, it is not possible to distinguish small objects since they are obscured by the structures of larger objects; e.g. bones. This drawback has been overcome to some degree by the development of body-section radiography techniques known as X-ray tomography.

Radiographic transverse tomography attempts to view sections or "slices" which are perpendicular to the axis of a patient. In a "classical" transverse tomographic system, incident X-radiation is passed through an object being studied at an angle and is imaged on a film. In order to image a particular slice, both the film and the object are rotated synchronously during the X-ray exposure. Shadows of points in a single plane of the object are continually projected onto the same place on the film during the rotation, whereas shadows of other parts of the object move in relation to the film. Thus, while the slice of interest is imaged relatively sharply, the resultant picture is overlayed by the motion-blurred images of other parts of the object. As a consequence, the resultant "tomogram" tends to lack contrast and fine detail is obscured.

Recently, digital processing techniques have been applied to the tomographic imaging problem and a degree of success has been achieved whereby blurred images of overlying and underlying planes have been removed so as to permit detection of greater detail. However, most digital methods require the processing of extremely large quantities of data, and even fast computers take significantly long times to do the necessary computations. Accordingly, commercial computer tomography equipment is extremely expensive and beyond the financial reach of many who desire it.

In another type of transaxial tomography, a narrow beam of X-rays is employed and only the rays passing through the desired cross-section are incident on a film so, ideally, only information about the particular slice is recorded. The result is a so-called "one-dimensional projection". A plurality of one-dimensional projections can be obtained by passing X-rays through the same cross-section at a number of different rotational angles. The resultant set of one-dimensional projections can be processed optically. Alternatively, the values of each projection can be fed to a computer for digital analysis, whereby the density function of each elemental area in the plane is computed by one of a number of mathematical techniques which utilize iteration, mathematical filtering techniques, and other known solutions.

An early technique for optical processing of a set of one-dimensional projections is disclosed in U.S. Pat. No. 2,281,931 wherein a cylindrical lens system is utilized to optically "enlarge" each one-dimensional projection in a direction perpendicular to the plane of the section. Each enlarged one-dimensional projection is a two-dimensional image and the set of two-dimensional images which result from optically enlarging each one-dimensional projection are superposed with mutual angular displacements that correspond to the rotation angles at which the one-dimensional projections were originally taken. The image ultimately produced in this manner has been referred to as a "layergram" of the cross-section. In recent years, attempts have been made to process the layergram using spatial filtering methods of both optical and digital natures to restore the layergram image which is known to suffer blurring. However, the digital processing techniques can again involve the handling and lengthy processing of large amounts of data, which is very expensive. Optical processing techniques toward this same end have generally been found to be either inadequate from a performance standpoint or unduly complex and expensive.

The techniques described in the above-referenced U.S. Pat. No. 2,281,931 is one of a number of image reconstruction techniques which utilize "back projection". Generally, the term "back-projection" implies that the value of a particular point in a projection is assigned to all points on a line perpendicular to the projection. The values of overlapping lines are integrated for all projections. The result is equivalent to back-projecting the values in each one-dimensional projection through the object and integrating their overall effect. As implied above, a simple back-projection yields results which are generally considered inadequate, and it is presently believed that a technique of back-projection, combined with a suitable filtering technique, could yield quality results. However, as emphasized above, such techniques have in the past generally required expensive and complex systems.

In the U.S. Pat. No. 4,023,036 there is disclosed a technique for generating a two-dimensional back-projected filtered image of a slice of an object. A carrier or film is provided with a plurality of substantially parallel elongated projections on the surface thereof, each projection having an optical characteristic representing the density characteristic of the slice of the object as measured at a particular relative rotational angle. Successive sinusoidal sections of the carrier are imaged and a photodetector is responsive to the imaged sections. Optical filtering is also performed. The filtered back-projected image is obtained by displaying as a video presentation the output of the photodetector. In one embodiment disclosed in this patent the carrier is in the form of a cylinder which is simultaneously rotated and tilted on its axis to achieve the desired imaging of sinusoidal sections of the carrier. In the U.S. Pat. No. 4,081,673 there is disclosed a related technique of optical back projection. In this case the projection-containing carrier or film referred to above (which is sometimes called a "sinogram") is processed using a special mask. The mask includes a plurality of cycles of a substantially sinusoidal shaped pattern of varying amplitude. The carrier and the mask are moved with respect to each other as individual elements of the back-projected image are reconstructed. Again, suitable optical filtering is employed. The mask may comprise a movable endless loop and the pattern thereon is a substantially sinusoidal transparency whose amplitude varies between zero and a predetermined maximum. Optical filtering may be implemented by providing the mask with an optical characteristic transverse the length thereof which corresponds to a predetermined filter function.

It is one of the objects of the present invention to provide another technique for generating a two-dimensional back-projected filtered image of a slice of an object.

The optical filter function utilized in optical back-projection techniques has both positive and negative components. Implementation of the bipolar filtering function has been performed and/or suggested in a number of ways. For example, assume that a given filter function curve h(x) is bipolar; i.e., has lobes above and below a zero level. If the entire filter function curve is translated by a constant amount to a higher reference level, the negative portions thereof would be above the zero level. If a filter is now constructed with transmittance, as a function of position, being represented by the translated curve, the transmittance would have only positive values. However, the video output obtained will be higher than it should be by the constant amount. Therefore, a video bias level can be employed to cancel the resultant "back-ground" brightness level. This technique has not proved to be completely satisfactory in operation. Various other schemes utilize separate filters or separate portions of the same filter for the positive and negative components, respectively, of the filter function. Separation into two discrete channels can be achieved using spatial separation, dichroic color separation, polarization separation, or other know techniques. Separate photodetectors are then employed for the two channels, and the output of the photodetector of the "negative" filtered channel is subtracted from the output of the "positive" filtered channel to obtain the desired video output. Again, the technique has not proved to be completely satisfactory in operation. The need for alignment and balancing of two channels is a limiting factor on performance.

It is a further object of the invention to provide an improved technique of optical filtering with a bipolar filter function.

DISCLOSURE OF INVENTION

The present invention is directed to an apparatus and method for generating a two-dimensional back-projected image of a slice of an object, and also to an optical filtering apparatus and method which, inter alia, is useful therein. In accordance with an embodiment of the apparatus of the invention, means are provided for generating successive beams of light, each having a narrow elongated cross-section with an optical intensity that is a function of the density characteristic of the slice of the object as measured at a particular relative rotational angle. The beams may be generated, for example, by successively illuminating individual one-dimensional optical projections, each having an optical characteristic that is a function of the density characteristic of the slice of the object as measured at a particular relative rotational angle. Means are provided for optically filtering the beams, and for spreading the beams in a direction transverse to their length. The optical filtering is preferably performed in accordance with a feature of the invention to be described hereinbelow. The spreading may be performed, for example, using a cylindrical lens. Two-dimensional electronic image sensing means, for example, a television camera, is provided for receiving the spread filtered beams. Means are also provided for effecting rotation between the beams and the image sensing means, the rotation being related to the relative rotational angles of the object associated with the generation of the successive beams of light. Further means are provided for accumulating the intensities sensed at elemental areas of the image sensing means. The accumulating means is preferably a digital frame store. The accumulated intensities comprise a two-dimensional back-projected image of the slice of the object which can then be displayed, for example, on a television display. An advantage of the described system over all-electronic digital processing is that the time consuming operations of filtering and back projection are performed optically. The digital subsystem need only be capable of adding and subtracting digitized frames of video. Dedicated hardware for this task is commercially available, and a large scale general purpose computing capability is unnecessary. Yet, the partially electronic nature of the processing can provide flexible advantages as compared to an all-optical system.

In a further form of the invention, there is set forth an apparatus and method for optically filtering a light beam with a filter function having a spatial characteristic that has both positive and negative components, and for producing an electronic representation of the filtered light beam. In an embodiment of the apparatus of this form of the invention, there is provided a first optical filtering means representative of the positive component of the filter function and a second optical filtering means representative of the negative component of the filter function. These two optical filtering means may be either two physically separate filter elements or, preferably, a single physical element which is switchable between two states that respectively serve as the first and second optical filtering means. Means are provided for alternately interposing the first and second filtering means in the path of the beam. Electro-optical sensing means which may be, for example, a television camera or a photo-detector (depending upon the type of system in which this form of the invention is employed), are provided to receive the filtered beam. Further means are provided for combining successive electronic outputs of the electro-optical sensing means. Finally, means synchronized with the interposing means are provided for controlling the polarity of the combining means. In an embodiment of this form of the invention, the first and second optical filtering means are electro-optically switchable, and the interposing means includes means for controlling the electro-optical switching of the filtering means. In one version of this embodiment, the controlling means includes a light polarizer and a polarization rotator, and the first and second optical filtering means together comprise a polarization sensitive element having first and second filtering states with respect to different polarizations of light incident thereon.

Further features and advantages of the invention will become more readily apparent from the following detailed description when taken in conjunction with the accompanying drawings.

BEST MODE FOR CARRYING OUT THE INVENTION

Figure 1:
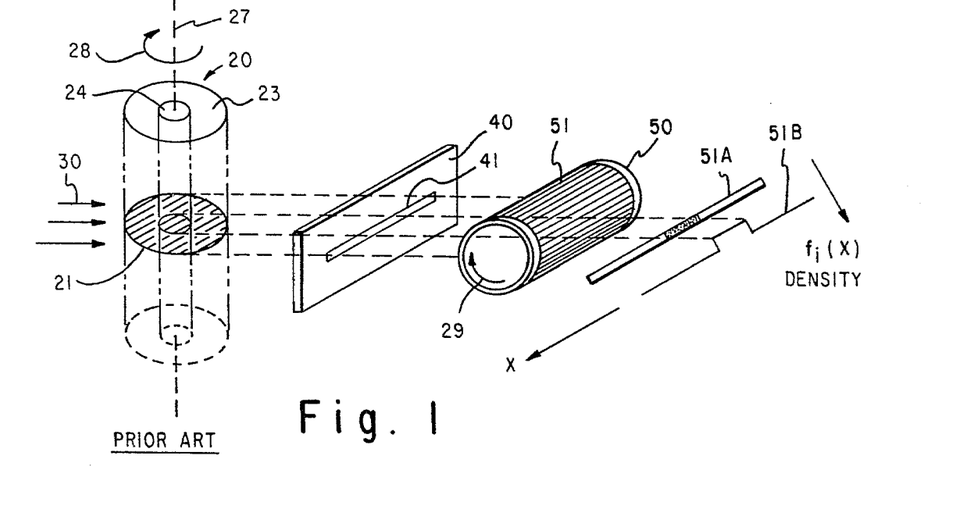
FIG. 1 is a diagramatic representation of a technique for generating one-dimensional projections of a slice of an object.

FIG. 1 illustrates the nature of one-dimensional projections of a body cross-section or slice which can be obtained, for example, in accordance with a technique forth in the above-referenced U.S. Pat. No. 2,281,931. A body 20, of which a cross-section 21 is to be reproduced, consists of an annular portion 23 of semi-transparent material, such as muscle tissue of a human limb, and a core portion 24 of a material which is less transparent to X-rays, such as bone. A beam of parallel X-rays 30 enamating from a remote source (not shown) passes through body 20, and a narrow portion of the X-ray beam, having a band-shaped cross-section, passes through a narrow elongated slot 41 in a diaphram 40, which is typically formed of lead. The X-ray beam passing through slot 41 produces a narrow elongated image 51 on X-ray sensitive film member 50, which is provided in the shape of a cylinder. The image 51 can be considered as a one-dimensional projection whose optical characteristic corresponds to the different degrees of absorption of the X-rays by the portions 23 and 24 of the body 20 at section 21.

The elongated strip 51A at the right of FIG. 1 illustrates a simplified version of the one-dimensional projection 51 which is recorded on film 50. It is seen that the central portion of the projection is darkest due to the low transmissivity of core 24 to X-rays and the resultant lesser exposure of the corresponding portion on film 50. (It should be noted that since the thickness of annular portion 23 increases toward the center, the overall transmissivity of this part will also decrease gradually toward the center of body 20 but, for ease of explanation, this gradation is not shown in the simplified illustration of strip 51A or the curve 51B which follows.) The curve 51B illustrates graphically the density function of the slice 21 as a function of length along slot 41, this length being indicated by the coordinate "x". The density, indicated as $f_i(x)$, is seen to correspond to the relative transmissivity of the cross-section as a function of x; i.e., the inverse of the density characteristic.

Returning to the structural portion of FIG. 1, the body 20, and consequently also the section 21 thereof, are rotated about an axis 27 which is normal to the plane of section 21 at the point of rotation, the rotation being represented by curved arrow 28. The cylindrical film 50, which is typically mounted on a drum, is rotated on its axis in angular synchronism with the rotation of body 20. At each of a number of discrete rotational positions, the body and the film 50 are stopped and a one-dimensional projection is recorded (like strip 51A). Accordingly, after a full 360° of rotation the cylindrical film 50 will contain a "set" of one-dimensional projections, i.e., the various $f_i(x)$, each one-dimensional projection having an optical characteristic which represents the density characteristic of the section or slice 21 of the object 20 as measured at a particular relative rotational angle. It will be understood that the one-dimensional projections may be a continuum on the film (e.g. made on a continuously moving film), but discretely recorded projections will be shown herein for ease of illustration.

Figure 2:
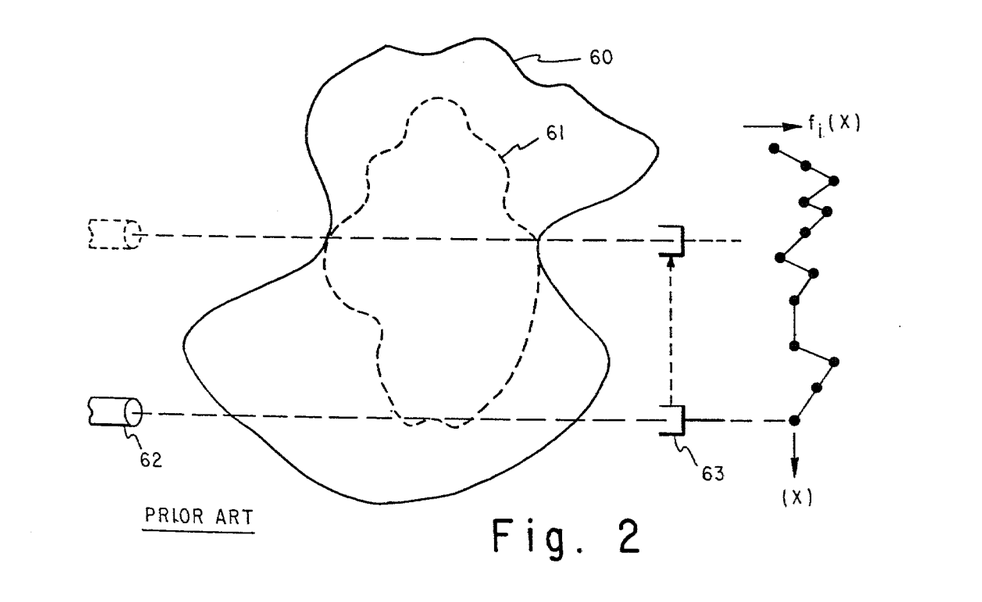
FIG. 2 shows another technique for obtaining one-dimensional projections of a slice of an object.

Referring to FIG. 2, there is shown another known technique of obtaining one-dimensional projections of a slice or section 61 of a three-dimensional body 60. A collimated "pencil" beam of X-rays is generated by a source 62, passed through the section 61, and received by a small-area scintillation detector 63, the output of which is indicated by a point on the graph at the right of FIG. 2. The source 62 and detector 63 are moved synchronously across the slice 61 and an output data value is obtained at each spaced position, each data point representing the intensity of the transmitted X-ray beam. The resultant function $f_i(x)$ is a one-dimensional projection similar in information content to those obtained using the system of FIG. 1, and as designated by the graph 51B of FIG. 1. It will be appreciated that, if desired, one could obtain an optical characteristic such as that of projection 51A from the data of FIG. 2 by utilizing the output of the detector 63 to modulate the intensity of a scanning beam exposing a film strip. More typically, the data points obtained from detector 63 are processed using a digital computer. A "set" of one-dimensional projections, $f_i(x)$, are obtained by taking the depicted measurements at a number of different rotational angles of the section 61, and the totality of the data is processed by a computer to attempt reconstruction of the elemental density function of the two-dimensional slice 61 of object 60. Further techniques for obtaining the desired one-dimensional projections are also set forth in the above-referenced U.S. Pat. No. 4,023,036.

Figure 3:
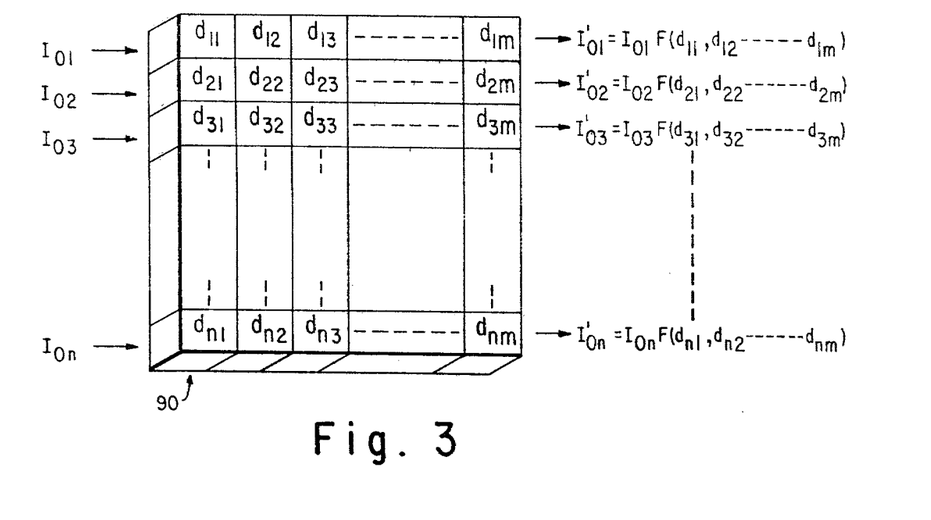
FIG. 3 is a diagram of a slice of an object useful in understanding approaches to obtaining the density characteristic of said slice.
Figure 5:
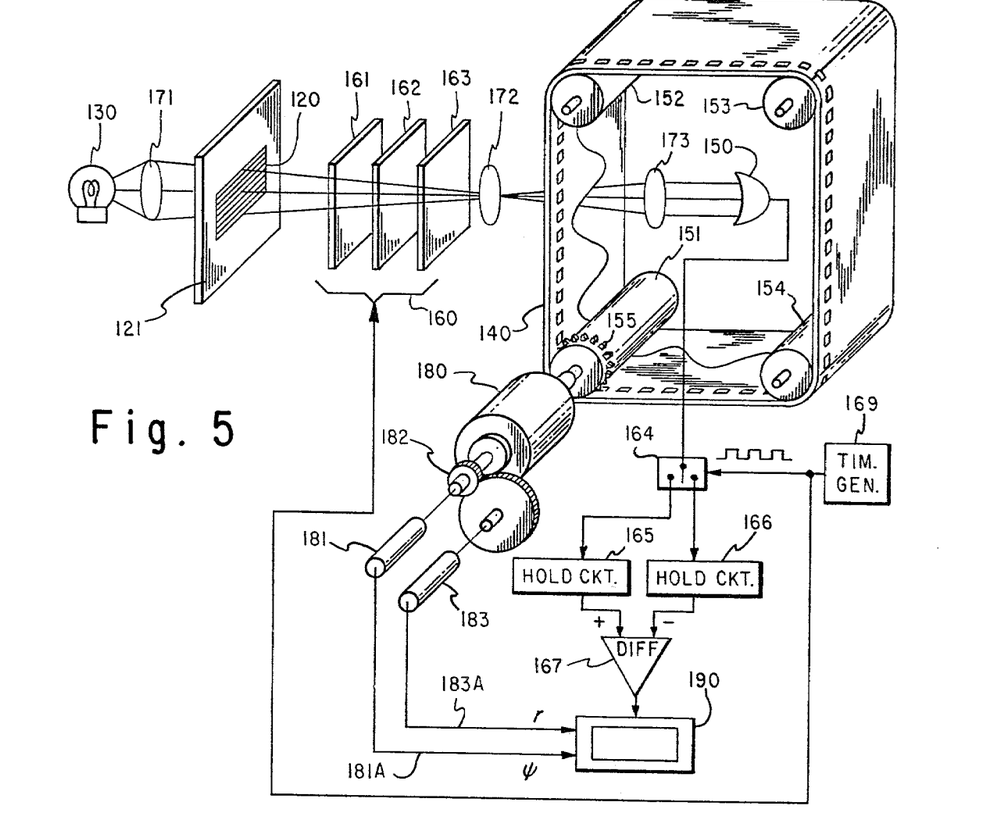
FIG. 5 is a schematic diagram partially in block form, of an embodiment of an apparatus which includes improvements in accordance with a form of the invention.

FIG. 3 is helpful in further illustrating the nature of the obtained one-dimensional projections, as well as in understanding approaches to obtaining the density characteristics of a section or slice of an object from such projections, and especially approaches which utilize "back-projection". A thin section or slice 90 under investigation is depicted as being rectangular for ease of explanation. The section is divided into an array of small elemental units which comprise an m by n array wherein each element is designated by its position in the array and assumed to have a density which is to be ultimately determined. Thus, for example, the density of the element in the upper left hand corner is designated by $d_{11}$, its adjacent neighbor to the right has a density designated by $d_{12}$, and so on. The beam, or portion of the beam (e.g. in FIG. 2 or FIG. 1), passing through a particular row of elements is designated by I with two subscripts, the first subscript indicating the reference angle at which the X-ray energy is passed through the slice 90 (a 0° reference angle is shown in FIG. 5, so the first subscript is 0), and the second subscript indicating the relative position of the particular beam or beam portion along the one-dimensional data coordinate (e.g. the x axis in FIGS. 1 and 2). The detected beams, or portions thereof, which have passed through the slice 90 are designated by primed versions of the input beams. Each output is equal to its corresponding input times a function of the elemental densities through which the beam or beam portion has passed. For example, it is seen that $I_{01}'$ is equal to $I_{01}$ times a function of the elemental densities of the first row of the array, as shown. Similarly, the remaining outputs are each also functions of the elemental densities in their corresponding rows. It will be appreciated that in the expressions for the one-dimensional projection values for a particular reference rotational angle (0° for the illustrated case), there are many more unknown than equations. However, if the slice is now rotated on its axis to a number of different positions, and additional one-dimensional projection data values are obtained at each rotational angle, the full "set" of one-dimensional projections will yield a large number of equations which can be used to approximate the unknowns; i.e., the individual elemental densities in the slice 90.

As referred to in the Background portion of the Specification, the set of one-dimensional projections can be processed by computer using various techniques. One type of prior art solution uses an iterative technique wherein assumed elemental density values are assigned to each member of the array. The computer calculates the output intensity values that would be obtained from the model, and these calculated output intensities are compared with the actual output intensities to obtain error values. The error values are examined and used to calculate appropriate modifications of the model which will yield smaller error values, and the process is continued until a model is obtained which yields error values that are considered acceptably small. Depending on the particular algorithm used, it will take at least some minimum number of computations for the model to "converge" to an acceptable state. In any event, the computer must have adequate speed, memory, etc., to obtain a solution within a resonable time, so the equipment needed can be prohibitively expensive. A number of techniques have also been attempted wherein the computer systematically solves the simultaneous equations by classical means or employment of known matrix manipulation methods. Unfortunately, these approaches are also found to require very large numbers of calculations and expensive computer equipment is needed for solution within practical time constraints.

In the "back-projection" image reconstruction technique treated above, the value of a particular data point in a projection is assigned to all points on a line perpendicular to the projection. In terms of FIG. 3, for example, the value $I_{01}'$ would be assigned to each of the elements in the row to which that output intensity is attributed; viz., $d_{11}$, $d_{12}$, ... $d_{1m}$. Similarly the output intensity value $I_{02}'$ is applied to all of the elemental densities in the second row; viz., $d_{21}$, $d_{22}$, ... $d_{2m}$, and so on for the remaining rows. Next, the output data values of the next one-dimensional projection are assigned in the same manner to each elemental density, and this is done for each relative rotation angle at which a one-dimensional projection was obtained. Thus, at the completion of the back-projection, each elemental density has a final value which equals the sum of all the data values attributable to it during the process previously described. The back-projection process can be performed either on a digital computer or optically, but the results of a simple back-projection have been found inadequate in most cases due to blurring.

Figure 4:
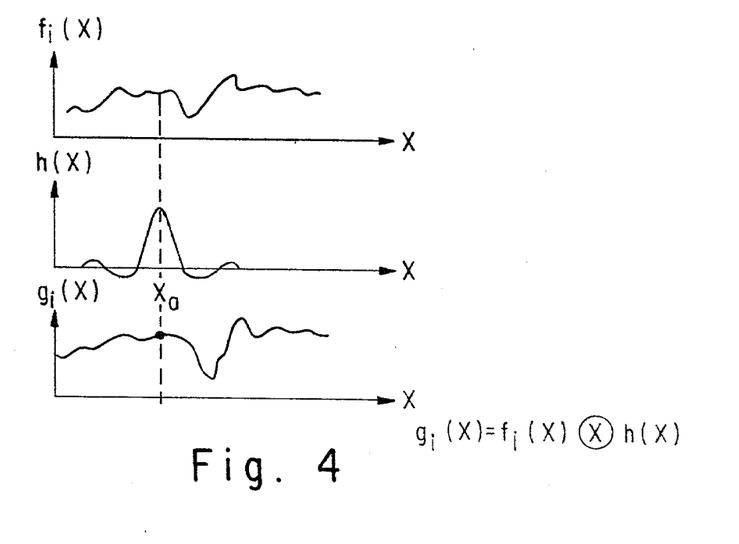
FIG. 4 shows graphs useful in describing the convolution of a filter function with a one-dimensional projection.

In order to derive better results using back-projection techniques, it is known that filtering can be used in conjunction with back-projection. The filtering can be visualized as a type of selective "weighting" which aids in restoration of a true density characteristic by removing blurring effects. FIG. 4 illustrates in general terms the filtering of a particular one-dimensional projection designated $f_i(x)$ using a filter function designed by $h(x)$. Mathematically, the two functions $f_i(x)$ and $h(x)$ are convolved to obtain the resultant filtered one-dimensional projection which is designated $g_i(x)$. For a symmetrical filter function, the convolution operation can be visualized graphically by considering the filter function $h(x)$ as being moved along the x axis and a multiplication between $f_i(x)$ and $h(x)$ being performed at each point of the excursion of the filter function. For example, in FIG. 4 the filter function is shown at an abscissa position $x_a$ and the resultant data point on the function $g_i(x)$ (as shown by the dot on the third graph) is obtained by multiplying $h(x)$ at this position by the function $f_i(x)$. This operation is performed at each point along the x axis and the function $g_i(x)$ is obtained in this manner. As disclosed in a publication of Cho et al in IEEE Transactions on Nuclear Science, Vol. NS-21, page 44 (June, 1974), one-dimensional projections are convolved with a processing function, as just described, the operation being performed on a digital computer. The actual implementation of filtering in accordance with an aspect of the invention, will be described hereinbelow.

Referring to FIG. 5, there is shown an embodiment of an apparatus which is generally of the type set forth in the above-referenced U.S. Pat. No. 4,081,673, but which includes improvements in accordance with the invention. A carrier or film 120 is supported in an opaque frame 121. The film has recorded thereon a plurality of substantially parallel elongated projection images, each projection image having a transmissivity which represents the density characteristic of a cross-section or slice of an object as measured at a particular relative rotational angle. The film 120 may be recorded in the manner described in conjunction with FIG. 1, or by using variations on the technique described in conjunction with FIG. 2 or in the above-referenced U.S. Pat. No. 4,023,036. Each projection is of the general type described with reference to the strip 51A in FIG. 1, and, in the present embodiment, the full 360° of arc of the film 120 contains adjacent projections taken at rotational increments of the object slice in question as it is rotated a full 360°.

Spaced from the film 120 is a movable mask 140 which, in the present embodiment, is in the form of an endless film loop mounted on a sprocketed roller 151 and idler rollers 152–154. A lamp 130 illuminates the film 120 and the light passing therethrough and through the mask 140 is incident on a photodetector 150. In the illustrated embodiment lens 172 images the projections on the film 120 onto the mask 140 and lenses 171 and 173 focus the light source at the detector. It will be understood, however, that various alternative optics can be employed.

The sprocketed roller 151 has a sprocket wheel 155 which engages sprocket holes on the edge of the mask film loop 140. A synchronous motor 180 drives the sprocketed roller 151 at a constant speed and a shaft encoder 181 generates an output signal 181A as a function of the roller position. Gearing 182 steps down the rotational rate of the roller 151 at a ratio to be described, and the rotation of gearing 182 is sensed by another shaft encoder 183 which generates an output signal 183A. Signals 181A and 183A synchronize the scan pattern of a display 190 (which could alternately be a recorder) which also receives the output of the photodetector 150 (via circuitry to be described) to modulate the brightness of the display. The resultant displayed or recorded image represents the filtered two-dimensional back-projected image of the slice of the object from which the one-dimensional projections on film 120 were originally made.

Figure 6:
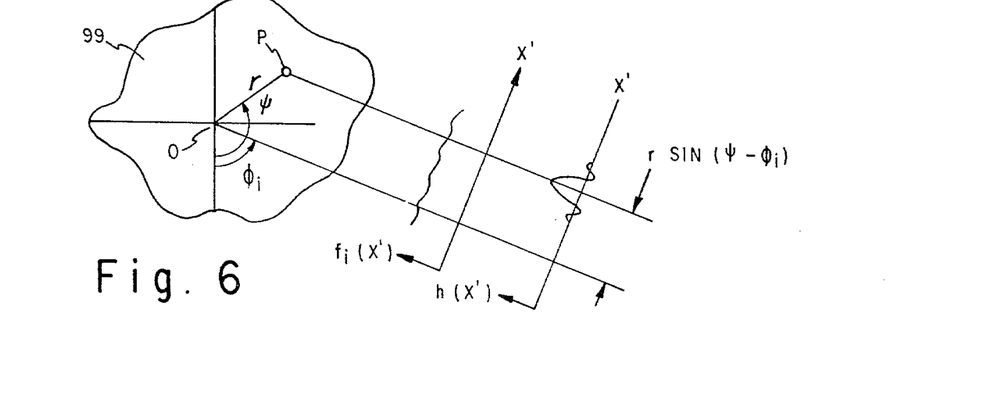
FIG. 6 is a representation of a slice of an object, along with explanatory graphs, which are useful in understanding the embodiment of FIG. 5.

The apparatus of FIG. 5, as described thus far, is in accordance with the apparatus disclosed in the above-referenced U.S. Pat. No. 4,081,673. An understanding of the overall operation thereof is facilitated by examining FIGS. 6 and 7. (Some of the mathematics relating to techniques of transaxial tomography disclosed herein is set forth in the above-referenced publication of Cho et al which describes the digital convolution of one-dimensional projections with a filter function.) Assume that $f_i(x)$ is the negative logarithm of a one-dimensional projection made at a reference rotational angle $\phi_i$, and assume further that the appropriate filtering function is designated $h(x)$ (see e.g. FIG. 4). A filtered projection can be represented by the following convolution integral:

$$\int_{-\infty}^{\infty} f_i(x-x')h(x')dx' \qquad (1)$$

The desired complete filtered image can be obtained, as previously discussed, by back-projecting each of the filtered projections into the object space and summing over all $\phi_i$. Mathematically, this operation is described by the sum $$\Sigma \left[ \int_{-\infty}^{\infty} f_i(x-x')h(x')dx' \right]_{x=r\sin(\psi-\phi_i)} \qquad (2)$$

where $(r,\psi)$ are the polar coordinates of a point in the object that is being reconstructed.

In the embodiment of FIG. 5 the mathematical operation of summation (2) is performed using a moving mask having a plurality of cycles of a substantially sinusoidally shaped pattern of varying amplitude, the integration being performed by the photodetector 150. Specifically, the mask 140 has N cycles of sinusoidally shaped transparency thereon which vary continually in amplitude from zero to a predetermined maximum.

Figure 7:
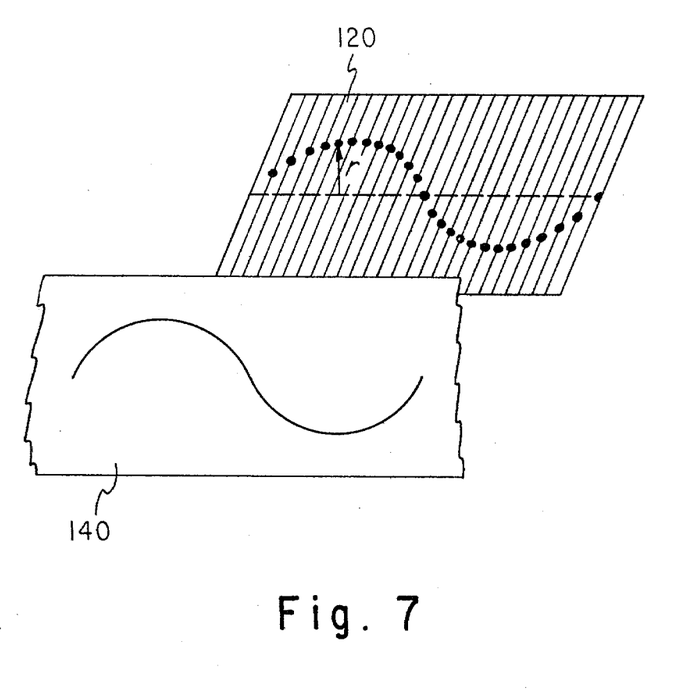
FIG. 7 is a simplified perspective representation of a mask imaging of a set of projections which is useful in facilitating understanding of the FIG. 5 embodiment.

The geometrical rationale can be better understood with reference to FIG. 7 which illustrates a portion of the mask 140 and one cycle of sinusoidal transparency thereof imaging the set of projections on the film 120. If the instantaneous amplitude of the sinusoid is designated r, it can be shown that a "point absorber" at a point $(r,\psi)$ in the original object (from which the projections 120 were made) would yield the illustrated sinusoidal pattern on the projections as the object is rotated through 360° of angles $\phi_i$ (see FIG. 6). Accordingly, the summation representative of each back-projected point of expression (2) is represented by the instantaneous output of photodetector 150. The relatively slow amplitude variation of the sinusoid is equivalent to varying the radius of the reconstructed point and the relatively fast phase variation of the sinusoid (image on the projections) is equivalent to varying the angle $\psi$ of the reconstructed point. These variations yield a spiral reconstruction pattern which is obtained on a display or recorder 190 by varying the radius of the scan in accordance with the signal 183A from shaft encoder 183 and varying the angular position of the scan in accordance with the signal 181A from shaft encoder 181. (If the display has conventional horizontal and vertical deflection means, the appropriate deflection signals are readily obtained from $r \sin \psi$ and $r \cos \psi$ respectively.) The circumference of the sprocketed roller 151 is set equal to the period of one cycle of the sinusoidal pattern on mask 140, so the output of the shaft encoder 181 varies directly with $\psi$, as desired. Gearing 82 steps down the rotational rate of the roller 151 by a factor of N. Since there are N cycles of sinusoid on the mask, the shaft encoder will cycle once for each complete cycle of the mask, and r will thereby vary directly with the sinusoidal amplitude, as desired. One type of technique for generating a mask having the desired varying sinusoidal pattern thereon is disclosed in the above-referenced U.S. Pat. No. 4,081,673.

The apparatus of FIG. 5 has been described thus far without reference to the filtering of the back-projected image. In the above-referenced U.S. Pat. No. 4,081,673, filtering is performed using the types of techniques described in the Background hereof. The embodiment of FIG. 5 utilizes an improved filtering technique which employs a filtering means 160. One form of the filtering means includes a birefringent polarization-sensitive element 163 which has two different filtering states, as will be described. The element 163 is located in the pupil plane of the optical system. The filtering means 160 operates under control of an electrical control signal 169A from a timing generator 169. The signal 169A, which may be a square wave at a suitable frequency such as 10 KHz, is also coupled to the control input of an electrically controlled solid state switch 164. The switch 164 receives as its input the output of photodetector 150. Switch 164 has two outputs which are respectively coupled to short time constant holding circuits 165 and 166. The holding circuit outputs are respectively coupled to the positive and negative input terminals of difference amplifier 167. The output of difference amplifier 165 is, in turn, coupled to display 190.

Operation, which will be described in further detail hereinbelow, is generally as follows: The filter means 160 is switched back and forth between two conditions which respectively represent the positive and negative components of the desired filter function. The switch 164 operates in synchronism with the switching of filter means 160 to couple the photodetector output, via holding circuit 165 or 166, to the positive or negative input terminal of difference amplifier 167. In particular, when the positive component of the filter means is interposed, the switch 164 is operative to couple the photodetector output to the positive input terminal of difference amplifier 167, whereas when the negative component of the filter means is interposed, the switch 164 is operative to couple the photodetector output to the negative input terminal of difference amplifier 167.

Before describing specific operation of the filtering performed, consideration of the theory underlying the structure of the present filtering means and the use thereof will now be set forth. Applicants have demonstrated that an appropriate filter function for transaxial tomography, such as the filter function illustrated in FIG. 4, can be synthesized by placing a Ronchi ruling in the pupil plan of one channel of a two-channel incoherent optical system. The method is applicable to an incoherent optical system that implements the so-called "convolution algorithm" for reconstruction from projections. In this algorithm, the one-dimensional projection data are first filtered by convolution with a one-dimensional filter function and then back-projected, as previously described herein, to form a two-dimensional image.

Although various filter functions may be used in this application, they have certain characteristics in common. In the frequency domain, useful filters have the general form $$H(\xi) = |\xi| A(\xi) \tag{3}$$

where $A(\xi)$ is a slowly varying apodizing function. In the space domain the filters consist of central positive cores surrounded by large negative sidelobes. We may write the filter function, $h(x)$, as the difference between two non-negative-definite functions:

$$h(x) = h_+(x) - h_-(x) \tag{4}$$

The positive part, $h_+(x)$, usually approximates a delta function while the negative part, $h_-(x)$, is somewhat more sensitive to the precise choice of $A(\xi)$. However, $h_-(x)$ will either fall off asymptotically as $1/x^2$ or execute oscillations with an envelope that falls off as $1/x^2$.

For example, consider the abrupt-cutoff filter for which $$A(\xi) = \text{rect}(\xi/2\xi_m) \equiv \begin{cases} 1 \text{ if } |\xi| < \xi_m \\ 0 \text{ if } |\xi| > \xi_m \end{cases} \tag{5a}$$

The corresponding filter function in the space domain is known to be $$h(x) = 2\xi_m^2 \text{sinc}(2\xi_m x) - \xi_m^2 \text{sinc}^2(\xi_m x) \tag{5b}$$

where $\sin c(u) \equiv \sin(\pi u)/\pi u$. This filter can yield an exact reconstruction (in the absence of noise) if the projection data are bandlimited with a bandwidth of $\pm \xi_m$ or less. For such data the first term in equation (5b) may be replaced by a delta function since convolving with $2\xi_m \sin c(2\xi_m x)$ is equivalent to multiplying the Fourier transform of the data by $\text{rect}(\xi/2\xi_m)$ and hence reproducing the original data. A decomposition of $h(x)$ into two non-negative parts can now be set forth as:

$$h_+(x) = \xi_m \delta(x), \tag{6a}$$

$$h_-(x) = \xi_m^2 \text{sinc}^2(\xi_m x). \tag{6b}$$

An incoherent optical implementation of this filter can be achieved using a two-channel system in which one channel has a large clear aperture and thus a point spread function ("PSF") approximately proportional to $\delta(x)$. The other channel has a pupil function in the form of a narrow slit of width $\xi_m \lambda f$, where f is the focal distance of the lens and $\lambda$ is the mean wavelength of the light. The PSF of this channel is readily shown to be proportional to $h_-(x)$ as given in equation (6b). Either an electronic or an optical attenuator can be used to adjust the constants of proportionality between the PSF's and the desired filter functions, while a differential amplifier can be used, as illustrated in above-referenced U.S. Pat. No. 4,081,673, to perform the subtraction operation necessary to achieve a bipolar filter function in an incoherent optical system.

A drawback of using a single slit is that the slit pupil will be rather narrow in practice and hence the light throughput of the negative channel will be small. This problem can be solved by replicating the pupil and using an array of many slits, i.e., a Ronchi ruling. The point spread function thus achieved is the irradiance in the Fraunhofer diffraction pattern of the ruling:

$$h_-'(x) \propto \sum_{n=-\infty}^{\infty} \text{sinc}^2(n/2) \cdot \text{sinc}^2[L(x/\lambda f - n/l)], \tag{7}$$

where L is the overall width of the pupil and l is the period of the ruling. (It is assumed that the ruling has a 50% duty cycle and that $L \gg l$.) The first sin c function in equation (7) specifies the intensity of each diffraction order. Note that $\sin c^2(n/2)$ vanishes for all even values of n except zero. For odd n, $\sin c^2(n/2) = (2/\pi n)^2$. The second sin c function in equation (7) describes the shape of the irradiance profile in each order. However, since it is assumed that $L \gg 1$, the orders are well separated and the precise shape of the profile is of little concern. We may thus treat the sin $c^2$ functions as delta functions and write $$h_-'(x) \propto \delta(x) + \sum_{n \text{ odd}} (2/\pi n)^2 \delta(x - n\lambda f/l). \tag{8}$$

To relate to the previous case of a single slit in the pupil plane, recall that the slit had a width of $\xi_m \lambda f$ while each transparent bar in the Ronchi ruling has width $l/2$. The various terms in $h_-'(x)$ can thus be equated with sampled values of $h_-(x)$, where the sample points occur at $x=0$ and $x=n\lambda f/l = n/2\xi_m$ (n=1,3,5 ...). The fact that $h_-'(x)$ is a sampled version of $h_-(x)$ is not surprising since sampling a function in the space domain corresponds to replicating that function in the frequency domain. The pupil function that led to $h_-'(x)$ was a replicated version of the pupil function for $h_-(x)$. Hence, the corresponding optical transfer functions, which are the autocorrelations of the pupil functions, bear a similar replicative relationship.

To complete the filter, one can either use a positive channel pupil of width L but with an intensity transmittance of 0.5, or can make the necessary adjustment electronically. The positive-channel PSF, $h_+'(x)$, is simply proportional to $\delta(x)$, with a constant of proportionality that makes its weight twice the weight of the $\delta(x)$ term in $h_-'(x)$. The overall function is then $$h'(x) = h_+'(x) - h_-'(x) \tag{9}$$

$$\propto \delta(x) - \sum_{n \text{ odd}} (2/\pi n)^2 \delta(x - n\lambda f/l).$$

Instead of using the two computed filters (i.e., filters representative of the components $h_+(x)$ and $h_-(x)$) in a two channel optical system, it can be advantageous to switch two filters alternately into the pupil plane of a single channel system. As demonstrated, for a two-channel system, the two "filters" that produce the desired result are a uniform pupil of a given (e.g. 50%) transmittance for the "positive" channel and a Ronchi ruling in the pupil for the "negative" channel. Therefore, for a single channel system, the desired result can be obtained by switching a Ronchi ruling into and out of the pupil plane of the imaging lens while simultaneously switching the effective polarity of the instantaneous contribution to the video output signal being produced. In a subsequent embodiment, to be described, a Ronchi ruling is, in effect, mechanically switched into and out of the pupil plane of a back projection system. Mechanical switching could also be employed in the FIG. 5 embodiment, but it is preferred to utilize the higher speed switching that can be implemented electro-optically. (It will be understood that there is a degree of common mode signal since the Ronchi will pass a zero order which corresponds to a fraction of the positive channel. However, it is the difference signal that is used to represent the desired filter.)

Figure 8:
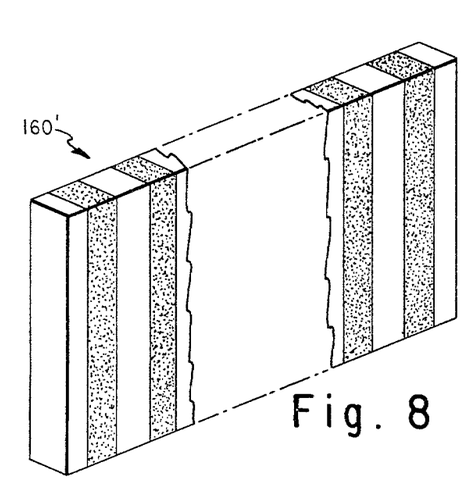
FIG. 8 illustrates an embodiment of a filter means which can be utilized in the FIG. 5 embodiment.

A number of electro-optical techniques can be used to effectively switch a Ronchi ruling into and out of the pupil plane of the system. As a first simplified example, FIG. 8 shows a filter means 160' for placement at the pupil in FIG. 5 (e.g. instead of 160) which comprises stripes of a liquid crystal material alternating with stripes of a transparent material. Electrodes, which can be applied by well known means, are not shown. For one polarity of the control signal 169A (FIG. 5), the liquid crystal stripes are transparent, so the aperture is substantially uniform. However, for the opposite polarity of control signal 169A, the liquid crystal stripes do not transmit, so the filter means appears to be a Ronchi ruling. Thus, at different times the filtering means 160' acts as a first filtering means (i.e., providing a uniform pupil) or a second filtering means (i.e., providing a Ronchi ruling at the pupil). The relative weighting of the inputs to difference amplifier 167 can be adjusted such that the positive input terminal inputs are applied with only half the weight of the negative input terminal inputs, thereby providing the desired effective uniform aperture at 0.5 transmittance for the positive filter component.

The Ronchi ruling interposed during the negative component filtering can, if desired, be a phase Ronchi, instead of an amplitude Ronchi (i.e., opaque stripes), as was the case for FIG. 8. The FIG. 5 embodiment, using a birefringent polarization-sensitive element 163 shown in FIG. 9, operates as a phase Ronchi for negative component filtering. In FIG. 5, filter means 160 includes a polarizer 161 which polarizes the received beam of unpolarized light in a given direction, for example, to produce vertically polarized light. The element 162 is an electro-optical polarization rotator that is operative, when activated by a given polarity of control signal 169A, to effect a rotation of the polarization of the light incident thereon by 90 degrees. When not activated, the rotator 162 has no effect on the polarization of light incident thereon. Therefore, the light output from polarization rotator 162 is either vertically polarized light or horizontally polarized light, depending upon whether a positive-going half-cycle or a negative-going half-cycle of control signal 169A is applied. The polarization rotator 162 may be, for example, of the type manufactured by Hinds International, Inc. of Portland, Oregon and known as a model JCK, although other types of polarization rotation schemes are known in the art.

Figure 9:
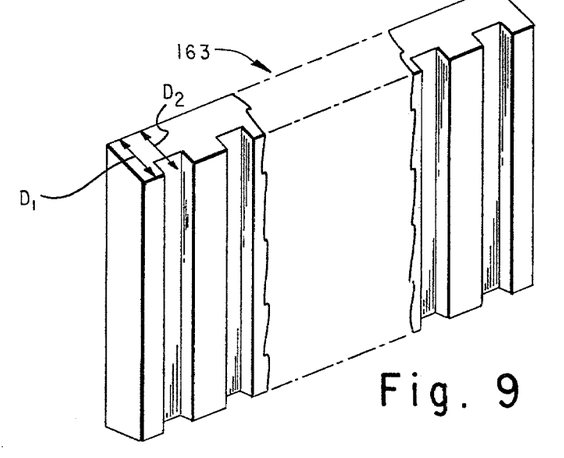
FIG. 9 illustrates an embodiment of filtering element which can be utilized in the FIG. 5 embodiment.

The element 163 is formed of a birefringent polarization-sensitive material, such as calcite. Element 163, an embodiment of which is shown in FIG. 9, has a rectangular wave profile formed, such as by etching, in a surface thereof. Calcite has the property of having different indices of refraction for different polarizations of light passing therethrough and, accordingly, will present a different indices of refraction to the vertically polarized light and the horizontally polarized light in the present embodiment. The depth of the grooves in element 163 are selected such that for one of the indices of refraction of the calcite, the difference between the two optical path lengths (i.e., the optical paths along the lines shown as $D_1$ and $D_2$, respectively, in FIG. 9) is an integral number of wavelengths, whereas, for the other index of refraction of the calcite, the difference between the two optical path lengths is an odd multiple of light half wavelengths. (It will be appreciated that the material in the grooves of element 163, e.g. air or oil, can be selected along with the groove dimensions to obtain the desired result.) Accordingly, for one polarization of the incident light, the element 163 does not introduce a phase shift to any portion of the light wavefront, whereas for the other polarization, the element 163 introduces 180° phase shifts in the manner of a phase grating. Therefore, as the control signal switches the polarization rotator 162, a phase Ronchi is effectively switched into and out of the pupil of the system. It will be understood that the polarizer 161 and polarization rotator 162 can be located at various other suitable positions in the optical system.

Other techniques, which would again employ elements 161 and 162 to obtain the switched polarization, can be used to effectively switch an amplitude Ronchi ruling in and out of the pupil (as was the case for FIG. 8). In one variation (not illustrated) the element 163 of FIG. 5 would be replaced by a polarization coded pupil. One-half of the pupil would be covered with a sandwich of a linear polarizer and an amplitude Ronchi ruling. The other half of the pupil would contain an orthogonal linear polarizer. As the polarization is switched, the effect is to switch between the two halves of the pupil (i.e., between the positive and negative filters). In another variation (not illustrated) the element 163 of FIG. 5 would be replaced by a "Vectograph" element (two layers of oriented PVA applied to opposite sides of a substrate) having a striped pattern thereon. "Vectrograph" materials are well known in the art and are manufactured by Polaroid Corp. The striped pattern of the "Vectograph" is operative to pass one polarization of the light, but does not pass the orthogonal polarization. Accordingly, as the polarization is switched, the effect is to switch a Ronchi ruling into and out of the pupil plane. In this, as well as in other described embodiments, appropriate adjustment of the effective transmittance for the uniform pupil component of the filter can be implemented, as indicated above, via adjustment of the gain of the positive channel of the electronics.

Figure 10:
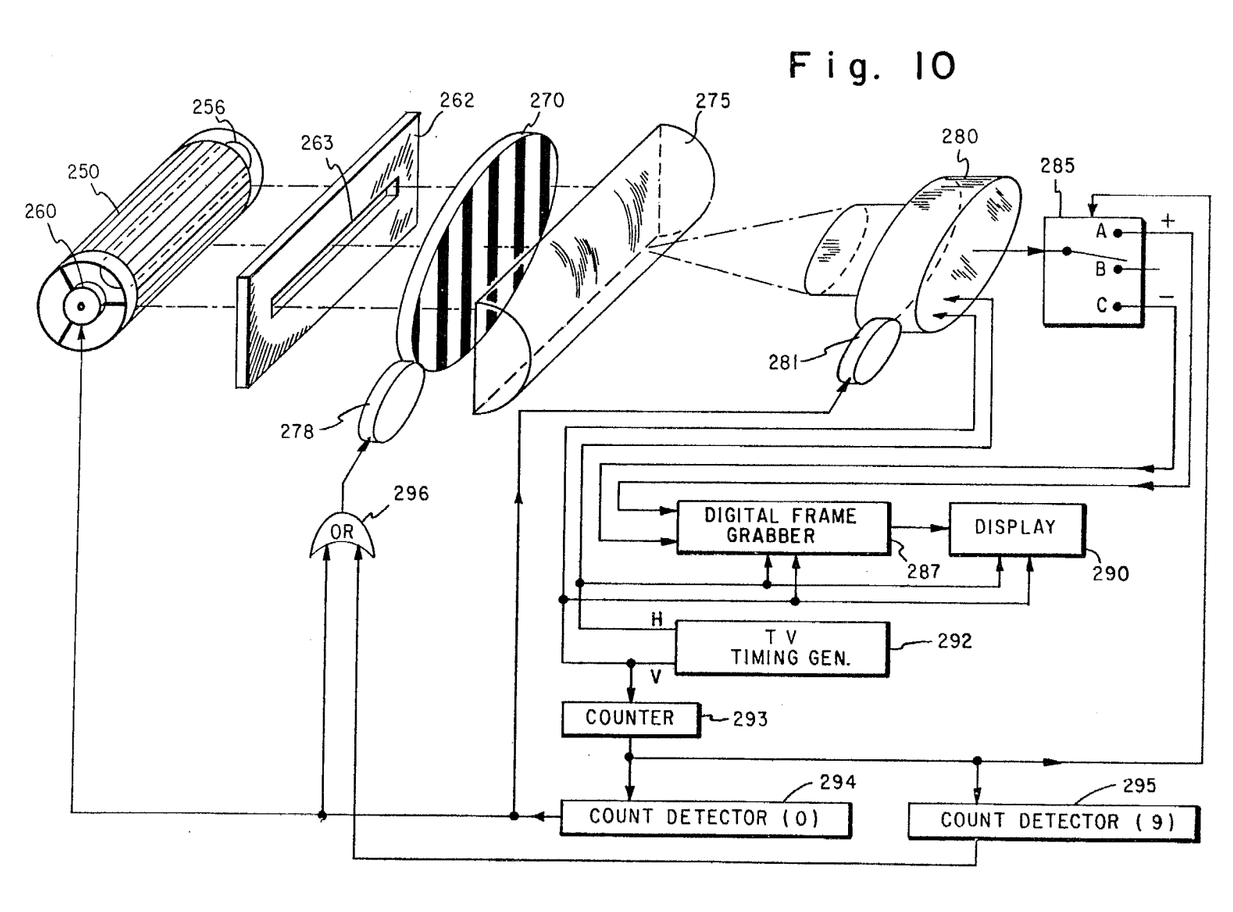
FIG. 10 is a schematic diagram, partially in block form of an embodiment of an apparatus in accordance with another form of the invention.

Referring to FIG. 10, there is shown a schematic diagram, partially in block form, of an embodiment of an apparatus in accordance with another form of the invention. A carrier or film 250 is similar to the film 120 of the FIG. 5 embodiment and may be formed in the manner described in conjunction with FIG. 1. The film 250 has a plurality of substantially parallel projections are optical representations of the density characteristic of a slice of the body 20, measured at successive relative rotational angles of the body. In the present embodiment, the film 255 is mounted on the surface of a translucent drum 255 that is adapted to rotate on its axis. The drum is illuminated internally by a light source 256. A stepping motor 260 is mechanically coupled to the drum at a drive ratio selected such that each step of the stepping motor rotates the drum by an increment equal to the distance between successive one-dimensional projections thereon.

Disposed in front of the drum is an opaque barrier 262 having a slit 263 therein, the slit being dimensioned such that the light from one of the illuminated elongated optical projections passes through it. Accordingly, the light beam emanating from the slit is an elongated beam having a cross-section whose intensity characteristic is a function of the density characteristic of the slice of the body as taken at the particular relative rotational angle. (It will be understood that alternative techniques could be used for obtaining the successive elongated beams of light; e.g. by generating them directly from the x-ray information taken at successive rotational angles through the slice of the body, without the intervening operation of recording the optical information on film.)

Disposed in the path of the elongated beam is a pupil plane filter means 270 and a cylindrical lens 275. The pupil plane filter means of the present embodiment is a Ronchi ruling which is mounted for 90° rotation. Another stepping motor 278 is utilized to obtain the successive 90-degree rotations of the filter 270. The filtered elongated beam is smeared in the vertical direction by cylindrical lens 275 and imaged onto the sensing surface of an electro-optical image sensor 280. The image sensor 280 may be of any suitable two-dimensional image sensing device, for example, a CCD image sensing device or camera which converts an optical image into an electronic video signal. The camera 280 is mounted for rotation on an axis perpendicular to the center of its image sensing screen. Still another stepping motor 281 is mechanically coupled to the camera and is operative to step the camera position to successive relative rotational angles in synchronism with the stepping to successive one-dimensional projections by stepping motor 260.

The output of camera 280 is coupled via a digitally controlled switch 285 to one of three terminals A, B or C. Terminal B is open circuited, and terminals A and C are respectively coupled to positive and negative input terminals, respectively, of a video frame grabber 287. The frame grabber 287 may be any suitable video frame storage medium or frame buffer (preferably digital) which includes the capability of adding to or subtracting from a stored video frame the elemental pixel values representative of the intensity or brightness of an image at each elemental area of the image. In other words, a resultant frame of video information stored in the unit 287 is a composite, at each elemental pixel region, of the sum of contributions to that pixel region from a plurality of video frames generated by video camera 280. The frame grabber may be, for example, of the type manufactured by Grinnell Systems of San Jose, California, and identified as the Model GRM-27. The GMR-27 digitizes an image and can store a digital image of 512×512 pixels, each pixel being represented by twelve bits of information. The output of frame grabber 287 is coupled to a video display 290, which may be any suitable television-type display. Alternatively, display may be implemented after video recording of the output of frame grabber 287.

The stepping motors 260, 278 and 281, as well as the digitally controlled switch, are controlled in synchronism by timing circuitry which includes a television timing generator, a count-to-seventeen counter 293, and a pair of count detectors 294 and 295. The television timing generator 292 provides vertical and horizontal synchronizing signals to the camera 280, the frame grabber 287, and the display 290. The vertical synchronizing signal, which may, for example, be at a frame rate of 30 frames per second, is coupled to the count-to-seventeen counter 293 which generates a digital output count that is coupled to digitally controlled switch 285 and to the count detectors 294 and 295. The counter 293 counts video frames to seventeen and then is automatically reset to zero and starts counting again. The count detector 294 generates an output signal upon detecting a zero count from counter 292. The output of count detector 294 is coupled to stepping motors 260 and 281, and also to one input of OR gate 296 whose output is, in turn, coupled to stepping motor 278. The count detector 295 generates an output signal upon detecting the count nine from counter 293. The output of count detector 295 is the other input to OR gate 296. The digitally controlled switch 285, which may be, for example, a multiplexer/demultiplexer, is operative to couple the switch wiper to contact A for digital inputs from one to eight, to couple the switch wiper to contact C for digital inputs from ten to seventeen, and to couple the switch wiper to contact B for digital inputs of zero or nine.

Overall operation of the embodiment of FIG. 10 is as follows: The stepping motors 280 and 281 step in synchronism so that each one-dimensional projection is back-projected in association with the appropriate relative rotational angle of the camera 280. Stepping of motors 280 and 281 are stepped every eighteen frames by the output of count detector 294. The incremental angular movement of the camera is the same as incremental angular movement of the body with respect to the source of radiation when originally generating the one-dimensional projections. Thus, it will be understood that a back-projected image is formed by storing the successive vertically smeared one-dimensional projections in cumulative fashion. The stepping motor 278 which controls rotation of the Ronchi ruling 270, is stepped every nine frames (i.e., at the counts of zero and nine) via OR gate 296.

During the frames when any rotation is taking place (i.e., frames or counts zero and nine of an eighteen frame cycle), the output of camera 280 is coupled to the open-circuited terminal B of switch 285, so nothing is stored by frame grabber 287.

During frames (or counts) one through eight, the Ronchi ruling is oriented with its stripes parallel to the beam elongation direction. This has no effect on the beam intensity as a function of its length. Since the beam is smeared in the direction perpendicular to its length, the Ronchi acts as a uniform pupil of 0.5 transmittance; i.e., the desired result for the positive component of the filter function as described above. In this filtering state eight video frames are added to the image stored in the frame grabber by virtue of the wiper of switch 285 being coupled to terminal A.

During frames (or counts) ten through seventeen, the Ronchi ruling is effectively in the optical path; that is, oriented with its striped pattern perpendicular to the beam length. As described above, this simulates the negative portion of the filter function. For this part of the cycle the wiper of switch 285 is coupled to terminal C, so eight frames are subtracted from the image stored in frame grabber 287.

The described cycle is performed for each one-dimensional projection, and the resultant image in the frame grabber 287 is a filtered back-projected image that can be presented on display 290. The number of video frames which are stored for each one-dimensional projection can be selected, in accordance with other system parameters, for optimum performance.

Figure 11:
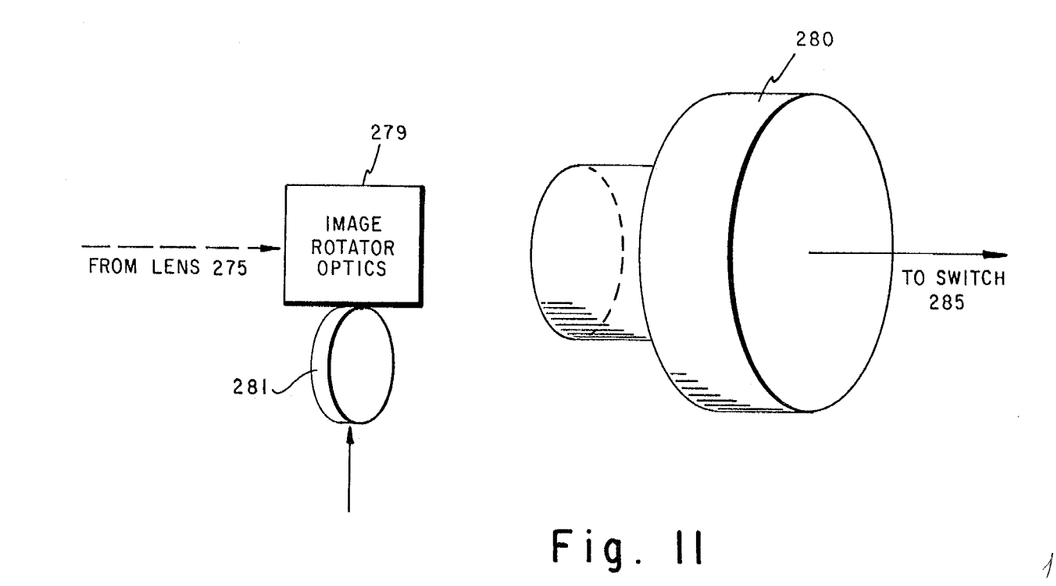
FIG. 11 illustrates a variation of the FIG. 10 embodiment.

In FIG. 11 there is shown a variation of the embodiment of FIG. 10 wherein the camera 280 is stationary and image rotator optics 279 are used to effect relative rotation between the optical beams and the camera 280. The image rotator optics, which is stepped by the stepping motor 281, may comprise a Dove prism, as described in "Applied Optics—A Guide To Optical System Design" by Leo Levi and published by J. Wiley, 1968.

The invention has been described with reference to particular embodiments thereof, but variations within the spirit and scope of the invention will occur to those skilled in the art. For example, the Ronchi ruling of FIG. 10 could be alternately switched into and completely out of the optical path, or electro-optical switching thereof could be implemented as in FIG. 5. Also, it will be understood that the synchronized operation of FIG. 5 can be implemented by alternative means, such as by providing pulse generation to drive a stepping motor (instead of the illustrated synchronous motor) as well as the display.

We claim:

1. Apparatus for generating a two-dimensional back-projected filtered image of a slice of an object, comprising:
    photodetector means;
    illuminating means directed toward said photodetector means;
    carrier means disposed between said illuminating means and said photodetector means, said carrier means having a plurality of substantially parallel elongated projections on the surface thereof, each projection having an optical characteristic representing the density characteristic of said slice of the object as measured at a particular relative rotational angle;
    mask means also disposed between said illuminating means and said photodetector means, said mask means comprising a plurality of cycles of a substantially sinusoidally shaped pattern of varying amplitude;
    means for moving said carrier means and said mask means with respect to each other;
    a light polarizer and a polarization switcher disposed between said illuminating means and said photodetector means;
    a polarization sensitive element disposed between said carrier means and said mask means, said polarization sensitive element having first and second filtering states with respect to different polarizations of light incident thereon;
    means synchronized with said polarization switcher for combining successive outputs of said photodetector means with opposite polarities; and
    display means responsive to the output of said combining means for displaying the back-projected image.

2. Apparatus as defined by claim 1 wherein said first and second filtering states are respectively positive and negative components of a filter function.

3. Apparatus as defined by claim 1 wherein said substantially sinusoidally shaped pattern is a sinusoidal transparency.

4. Apparatus as defined by claim 2 wherein said substantially sinusoidally shaped pattern is a sinusoidal transparency.

5. Apparatus as defined by claim 3 wherein said mask means comprises a movable endless loop.

6. Apparatus as defined by claim 4 wherein said mask means comprises a movable endless loop.

7. Apparatus as defined by claim 3 wherein said display is synchronized with said moving means.

8. Apparatus as defined by claim 4 wherein said display is synchronized with said moving means.

9. Apparatus for optically filtering a light beam with a filter function having a spatial characteristic that has both positive and negative components, and for producing an electronic representation of said filtered light beam, comprising:
    a light polarizer and a polarization switcher disposed in the path of said beam;
    a polarization sensitive element disposed in the path of said beam, said polarization sensitive element having first and second filter states which respectively represent said positive and negative components of said filter function;
    electro-optical sensing means for receiving the filtered beam;
    means for combining successive inputs to said electronic electro-optical sensing means; and
    means synchronized with said polarization switcher for controlling the polarity of said combining means.

* * * * *